United States Patent [19]

Hixson, Sr.

[11] Patent Number: 5,040,198

[45] Date of Patent: Aug. 13, 1991

[54] MAMMOGRAPHIC SPOT COMPRESSION AND MAGNIFICATION DEVICE

[75] Inventor: Gordon L. Hixson, Sr., Chattanooga, Tenn.

[73] Assignee: American Mammographics, Inc., Chattanooga, Tenn.

[21] Appl. No.: 591,563

[22] Filed: Oct. 2, 1990

[51] Int. Cl.$^5$ .......................... A61B 6/04; H05G 1/00
[52] U.S. Cl. ..................................... 378/37; 378/208; 378/209
[58] Field of Search ................... 378/37, 20, 177, 178, 378/179, 180, 195, 208, 209, 210

[56] References Cited

U.S. PATENT DOCUMENTS 4,156,145  5/1979  Weatherholt ...................... 378/208

FOREIGN PATENT DOCUMENTS 2014151 12/1971  Fed. Rep. of Germany ........ 378/37

*Primary Examiner*—Edward P. Westin
*Assistant Examiner*—Don Wong
*Attorney, Agent, or Firm*—Alan Ruderman

[57] ABSTRACT

A spot compression and magnification device for use with mammographic units to aid in the spot compression of a female patient's breast to obtain a high degree of focal breast compression and a high quality x-ray image of a suspicious mass within the breast. The device is positionable on the image platform of a conventional mammographic unit and has a base including an open bottom and an upstanding pedestal opening into the base, the pedestal having a flat top surface so that an air gap is provided between the top surface of the pedestal and the surface of the imaging platform. The device is constructed from a synthetic plastic material of sufficient rigidity and having low x-ray absorptivity. The base has excluded material in the form of an opening to increase the flexibility of the device to permit increased depression of the top of the pedestal facing the patient. The pedestal has a substantially truncated conical form while the base has a substantially rectangular cross sectional configuration. Three embodiments of the device are illustrated, each of which is of a substantially different size to provide different magnifications.

22 Claims, 2 Drawing Sheets

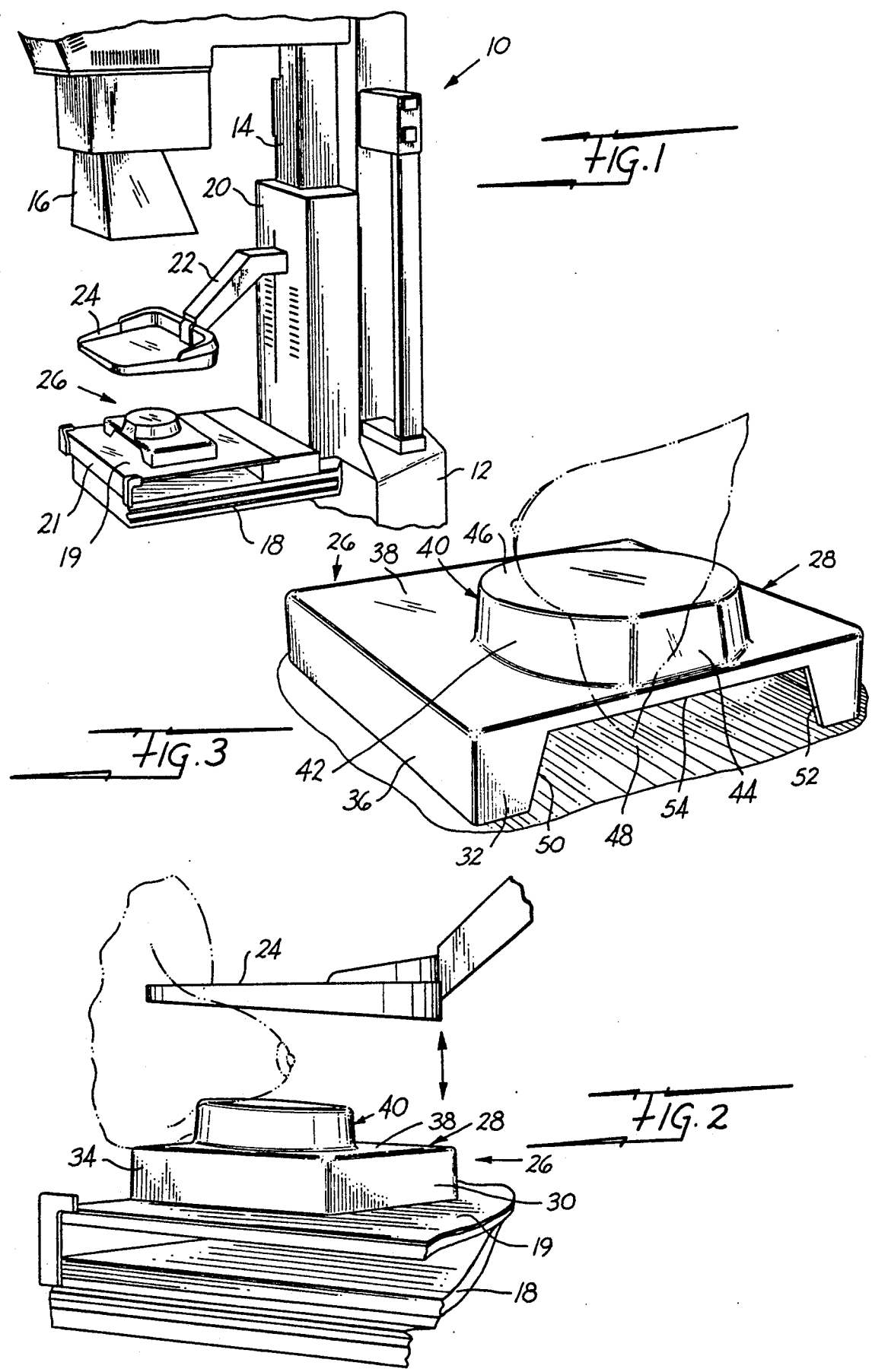

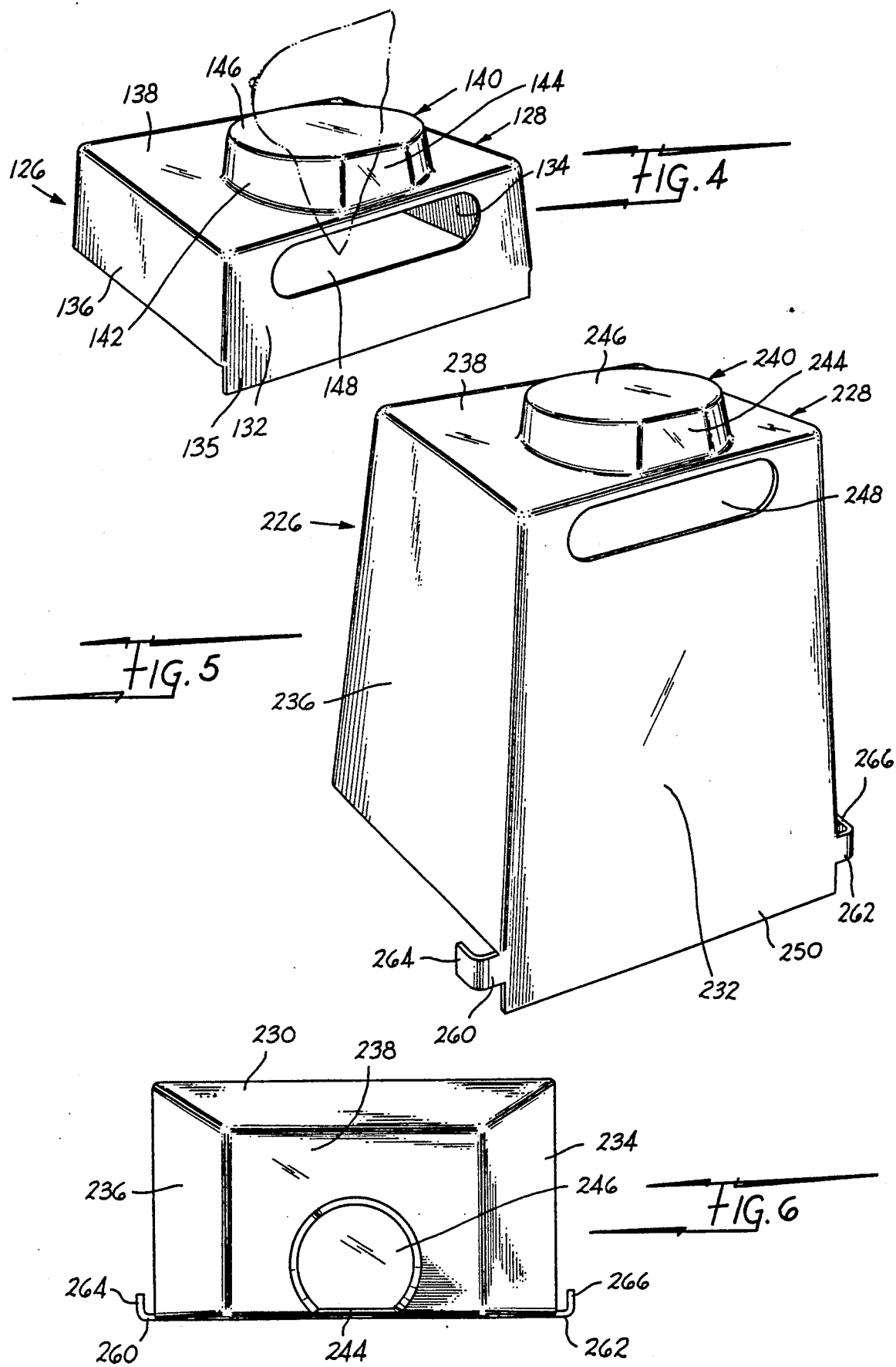

MAMMOGRAPHIC SPOT COMPRESSION AND MAGNIFICATION DEVICE

BACKGROUND OF THE INVENTION

This invention relates to mammography and more particularly to a spot compression and magnification device for aiding in compressing a small area of the breast of a woman undergoing a mammographic examination to displace glandular structure and enhance the quality of the image made by the mammography x-ray apparatus.

The x-ray evaluation of the breast, known as mammography, can provide a sensitive and satisfactory means for examining women when screening for breast cancer, an abnormality which affects a significant percentage of the female population. The predictability of the results of the procedure, which is predicated upon an interpretation of the x-ray image produced, and thus the quality of the image, may in certain cases be indefinite and thus inconclusive. For example, many of the abnormal or suspicious soft tissue densities demonstrated are neither clearly benign nor malignant. Cancers, benign tumors, cysts, and asymmetrical areas of glandular tissue can all have similar appearances. Consequently, breast biopsies subsequent to mammographic examination using conventional compression of the breast disclose a relatively low positive yield for cancer, ranging from ten percent to thirty percent. Thus, it has been demonstrated that equivocal mammographic abnormalities require supplemental diagnostic procedures to avoid unnecessary breast biopsy.

One of the most useful additional procedures is a spot compression view which is performed with a small compression paddle to compress only a small area of the breast to increase the accuracy of the image and confidence of the interpretation, the small compression paddle being substituted for a larger conventional paddle. A spot compression view spreads apart glandular structures which can simulate a mass or hide the margins of a true mass. Such views can better define a mass seen on a routine view, and also distinguish abnormalities from those caused by superimposition of normal breast tissue. In the majority of cases a spot compression view shows the suspicious soft tissue density to be benign thereby eliminating unnecessary additional mammographic examination necessitating an additional dose of x-rays, and/or breast biopsy.

Conventional mammographic views utilize a large flat compression paddle which is pushed against the upper portion of the breast to compress the breast between the paddle and the imaging platform of the mammography apparatus. The smaller compression paddle is conventionally used to compress a small area over a potential abnormality in the breast when spot compression views are performed. All of the known compression paddles in the prior art are mechanically attached for use to the adjustable vertical column of the mammographic unit above the breast. When a suspicious area is located on an x-ray, the standard paddle is removed and replaced by the smaller spot compression paddle, which as aforesaid provides a localized compression and a higher quality view by moving normal glandular structure or tissue from dispositions which may be superimposed relative to the area of the breast which requires closer examination.

Many of the older mammographic units in operation do not have the capability of readily accepting spot compression paddles which, it is believed, are available only for the newer mammographic units. Because of the enormous capital expense required for acquiring such units, many hospitals and other diagnostic facilities having the older mammographic units have not made, and may be unable to make, such expenditures as are necessary. Additionally, even with those newer units that have spot compression paddles, because of the normal shape of a breast, i.e., the upper portion of the breast has a greater slope than the lower portion which is substantially horizontal, compression of the breast at the upper portion against the imaging platform may not provide as much clarity to the image as would appear to be the case were the breast to undergo additional spot compression from the lower portion. At least one manufacturer provides a rigid stool-like member for increasing the magnification of the image, but not for spot compression of the breast, the member being attachable to the image platform and having a large top portion on which the breast rests while the image is being made.

SUMMARY OF THE INVENTION

Consequently, it is a primary object of the present invention to provide a spot compression and magnification device for use with mammographic apparatus for aiding in localized compression of the breast of a woman patient to obtain x-ray images of a quality providing procedural results of reliable predictability.

It is another object of the present invention to provide a spot compression and magnification device positionable on the imaging platform of a mammographic unit and adapted to support a breast of a woman which is compressed between the device and a conventional compression paddle.

It is a further object of the present invention to provide a spot compression and magnification device interposed between the breast of a female patient and the imaging platform of a mammographic unit, the device having a base positionable on the imaging platform and an upstanding pedestal on which the breast is positioned, the geometric configuration of the pedestal providing a high degree of focal breast compression, the device being depressible to produce relatively greater thinning of the breast at the nipple and subareolar area and to conform to breasts of various shapes and sizes as the breast is compressed between the device and a conventional paddle pressing on the upper surface of the breast.

It is a yet still further object of the present invention to provide a spot compression device interposed between the breast of a female patient and the imaging platform of a mammographic unit, the device having a base positionable on either the imaging platform or directly upon the cassette within which x-ray sensitive film is carried, and an upstanding pedestal upon which the breast is positioned, the device having low radiation absorptivity and providing an air gap between the breast and the imaging platform for improving radiographic contrast resolution and increased magnification.

Accordingly, the present invention provides a device as accessory for mammographic units for aiding in the spot compression of a female patient's breast to obtain a high degree of focal breast compression and variable degrees of magnification and thus to provide high quality x-ray images or views of a mass in the patient for greater diagnostic predictability. The device is free standing in that it is positionable upon the imaging platform of a conventional mammographic unit, or directly upon the cassette within which x-ray sensitive film is carried requiring no mechanical attachment thereto, and comprises a base having an open bottom and an upstanding pedestal opening into the base and having a peripheral wall extending from the upper surface of the base. The base has means, preferably in the form of excluded material, to increase the flexibility of the device for permitting increased depression of the portion of the pedestal facing the patient so as to produce relatively greater thinning of the breast at the nipple and subareolar area as opposed to posterior aspects of the breast. The breast is positioned on the pedestal and is compressed between the device and a conventional mammographic paddle acting on the upper portion of the breast.

In the preferred form of the invention the base has a substantially rectangular cross sectional configuration and the pedestal has a substantially truncated conical form, the excluded material in the preferred embodiment being an opening formed in the upstanding wall of the base facing the patient. The air gap provided by the device between the imaging platform and the upper surface of the pedestal provides improved radiographic contrast resolution and magnification to the image. The device may have the base formed of different heights to provide devices of different magnifications. The device is formed from a transparent plastic material of sufficient rigidity to support a large breast without buckling, yet permitting the pedestal to depress by virtue of the excluded material, at least at the portion adjacent the patient, the material also having low radiation absorption characteristics.

BRIEF DESCRIPTION OF THE DRAWINGS

The particular features and advantages of the invention as well as other objects will become apparent from the following description taken in connection with the accompanying drawings, in which:

FIG. 1 is a fragmentary perspective view of a conventional mammographic unit with a spot compression device constructed in accordance with the principles of the present invention positioned on the imaging platform thereof;

FIG. 2 is a perspective view illustrating the spot compression device of FIG. 1 during use;

FIG. 3 is an enlarged perspective view of the device illustrated in FIG. 2 as viewed from the opposite end;

FIG. 4 is a view similar to FIG. 3, but illustrating another embodiment of the device with a greater degree of magnification;

FIG. 5 is a view similar to FIG. 4, and illustrating another embodiment of the device having a still greater degree of magnification; and FIG. 6 is a top plan view of the device illustrated in FIG. 5.

DESCRIPTION OF THE PREFERRED EMBODIMENTS

Referring now to the drawings, FIG. 1 illustrates a portion of a conventional relatively new type of mammographic unit 10, the unit comprising a frame 12 supporting a vertically adjustable column 14. The column 14 supports an overhanging head 16 which carries an x-ray source (not illustrated). Disposed below the head 16 is a vertically adjustable image platform 18, the platform generally having a cover member 19 disposed thereon and within which x-ray sensitive film is carried in, for example, a film cassette (not illustrated). Conventionally, the breast of a patient is placed on the cover member overlaying the film. Disposed about the column 14 is a housing 20 to which the arm 22 of a standard compression paddle 24 is attached. The arm may be vertically adjusted to lower the paddle 24 onto the upper portion of the breast to compress it against the cover member 19, the adjustment in at least some units being effected by pneumatic means. A small paddle with its own arm may be substituted for the standard paddle when conventional spot compression x-ray images or views are to be made of a suspicious area within the breast, the smaller paddle acting to concentrate or localize the compression force on a smaller area of the breast for a higher quality view as heretofore described. As aforesaid in many of the older mammographic units in current use spot compression paddles are not provided, nor are they readily available, and the units do not appear to have the capability of receiving such spot compression paddles. Accordingly, in these older units a spot compression view can not be obtained and the results of the procedure may be equivocal.

In accordance with the present invention, a spot compression device 26 constructed in accordance with one form of the invention, is disposed on the cover 19 of the platform 18 over the window, and the compression paddle 24, either a standard or a spot compression paddle in those units having same, is lowered onto the breast 28 to compress the breast between the device 26 and the paddle 24 to obtain a high degree of focal breast compression. Thus, the device 26 of the present invention, and the subsequent embodiments hereinafter described, may be utilized with either the newer or older mammographic units, and in the latter case may provide spot compression capabilities not currently available for such units. As aforesaid, spot compression views are particularly significant for many patients.

As illustrated in FIGS. 2 and 3, the device 26 comprises a base 28 having a substantially rectangular configuration including a front skirt 30 and a rear skirt 32 spaced apart by a pair of spaced apart end skirts 34, 36. The base, which is open at the bottom, includes an upper surface 38 having an aperture (not illustrated) formed therein, and a pedestal 40 is disposed on the upper surface overlying the aperture. The pedestal 40 is open at the bottom so as to open onto the interior of the base. Additionally, the pedestal 40 has a substantially truncated conical configuration with an upstanding peripheral wall 42. The peripheral wall 42 includes a flat rear portion 44 with the remaining portion being substantially circular, a substantially flat upper surface 46 being disposed on the top of the wall 42 and conforming to the peripheral configuration thereof. Thus, when the device 26 is disposed on the cover member 19 of the platform 18, the upper surface 46 of the pedestal 40 has a clear path to the cover member, thereby providing an air gap between the surface 46 and the cover member. Alternatively, the device may be disposed directly on the x-ray film cassette. The disposition of the pedestal is such that the bottom of the flat wall portion 44 may be very slightly offset from the rear skirt 32 of the base, or may be substantially aligned with the upper edge of the rear skirt 32, and although this disposition may vary slightly according to manufacturing methods and tolerances, it is important that the flat rear wall portion be disposed closely to the plane of the skirt 32 so as to abut the chest of a patient beneath the breast.

Moreover, the rear flat wall portion 44 of the pedestal has a slight slope, in the order of approximately two degrees, flaring outwardly further at the bottom than at the upper surface 46. The remainder of the wall 44 has a downward slope in the order of approximately seven degrees so that the cross sectional configuration of the pedestal is larger at the junction with the surface 38 of the base than at the upper surface 46 so as to provide a localized compression of the breast when the breast is compressed between the upper surface 46 and the paddle 24.

Formed in the rear skirt 32 is an area of excluded material, preferably in the form of an opening 48 spaced inwardly from the end skirts 34, 36. The opening 48 at the upper border thereof, in a small compression device such as illustrated in FIGS. 2 and 3, is spaced slightly beneath the upper surface 38 of the base and extends to the lower edges of the remaining portion of the skirt 32. This opening 48 provides the device with the flexibility to permit depression of the back portion of the pedestal 20 and a greater degree of compression of the posterior aspect of the breast thereby producing a relative increase in thinning of the breast at the nipple and subareolar area.

The compression device 26 preferably is formed from a synthetic plastic material, and it has been found that a transparent copolyester such as polyethylene Terephthalate-Glycol-modified such as that sold under the trademark KODAR by Eastman Chemical Company of Kingsport, Tenn. has provided satisfactory results. Another material under consideration is polycarbonate such as that sold under the trademark LEXAN sold by General Electric Company. These materials not only have a relatively high tensile strength, but have low x-ray radiation absorption characteristics. A small spot compression device 26, such as that illustrated in FIGS. 2 and 3, may be molded from the aforesaid material in two portions, the base forming one portion and the pedestal the other portion, with the two portions subsequently bonded together by a conventional adhesive. Representative dimensions of a device 26 constructed in accordance with the present invention provides a base 28 having the length of the front and rear skirts 30, 32 in the order of approximately 4½ inches, the end skirts 34, 36 in the order of approximately 3½ inches, the height of the skirts in the order of approximately ⅞ of an inch and the nominal wall thicknesses of the base in the order of approximately 1/24 of an inch (e.g. approximately 1 mm). The height of the opening 48 from the bottom edges of the skirt 32 may be approximately ⅝ of an inch with a length of approximately three inches at the bottom. As illustrated, the opening 48 may have flared or angularly disposed end borders 50, 52 which taper downwardly so that the distance at the upper border 54 is smaller than the distance between the end borders 50, 52 at the lower edges of the skirt 32, the distance between the end borders 50, 52 at the top being in the order of approximately 2½ inches in the device described. The flaring of the borders 50, 52 of the opening 48 permits relatively high compression of the device while maintaining sufficient rigidity, i.e., it provides a large lateral spacing between the borders without excessive weakening thereof especially when compressed against a patient with large breasts. The pedestal 40 for this representative device has a height of approximately 11/16 inches, a diameter at the top surface 46 of approximately 2¾ inches excluding the flat wall surface 44 which is approximately 1½ inches in length so that the front to rear distance across the top surface 46 is in the order of approximately 2½ inches, the nominal wall thickness of the pedestal being approximately 1/32 of an inch or less. Thus, the total height of the device described, is approximately 1 9/16 inches which provides a magnification factor in the order of approximately 1.08. To preclude the device from moving over the platform when the chest of a patient abuts the rear skirt 32, the lower edges of the base may be coated with a high friction material.

In use, the device 26 is placed on the cover of the imaging platform with the center of the pedestal disposed in superposed relationship over the x-ray film. The breast of a patient is then placed on the pedestal with the mass under consideration centered over the center of the pedestal. Pressure is then applied to the upper portion of the breast with the compression paddle 24 compressing the breast between the compression paddle 24 and the device 26.

Accordingly, the device heretofore described permits depression of the rear of the pedestal so as to provide a relatively greater increase in thinning of the breast at the nipple and subareolar area and thus a substantial degree of compression of the posterior aspect of the breast. The air gap provided between the upper surface 46 of the pedestal and the imaging platform cover provides improved contrast resolution and increased magnification. Accordingly, since the device is free standing in that it is positioned o the imaging platform cover and requires no mechanical attachment to mammographic units, it may be utilized with any of the known mammographic units and experimentation has confirmed its ability to provide results to distinguish abnormalities from normal breast tissue in suspicious areas.

Another embodiment of the present invention is illustrated in FIG. 4, here a spot compression device 126 having a larger base 128 is provided for obtaining a greater degree of magnification than the device 26. The base 128 is substantially rectangular in form, but may have slight diverging slopes from the top surface 138 to the bottom edges of the respective skirts so as to have a somewhat truncated pyramid configuration, albeit the slope of the various skirts may be unequal. The rear skirt 132, in this embodiment, because of the increased height of the base, e.g. approximately two inches, does not have the opening 148 extending downwardly to the bottom edge of the skirt 132, which would reduce the rigidity of the device and weaken it excessively. Thus, the opening 148 is wholly confined within the skirt 132. Although the cross sectional configuration of the pedestal 140 is substantially identical to that of the pedestal 40 of the device 26, including a conical configuration having a flat surface 144 at the rear thereof and a circular configuration at the remaining portion of the upstanding wall 142, the height of the pedestal 140 is greater than that of the pedestal 40.

In this embodiment the front and rear skirts may be in the order of approximately 5½ inches with the end skirts in the order of approximately 4¼ inches, the height of the base being approximately two inches and the height of the pedestal approximately one inch. With these dimensions, the additional increase in the air gap between the bottom edges of the skirts and the top surface 146 of the pedestal increases the magnification factor to approximately 1.16. As aforesaid the skirts of the base have a slight downward slope which together with the opening 148 permits proper depression of the back of the pedestal when compressed by a breast. Although the slope of the skirts does not appear to be critical, it is preferred that the slope of at least the rear skirt 132 be in the order of approximately 6 degrees. Additionally, for this large a unit in order to more properly conform to the chest wall beneath the breast of the patient, the flat rear wall 144 of the pedestal may also have a downward slope of approximately that magnitude. With the above dimensions, it has been found that when the opening 148 has a length of approximately 3½ inches and a height of approximately ¾ of an inch, desirable results are obtained. The rear skirt 132 may have a downwardly depending lip 135 extending beyond the end skirts 134, 136 and the front skirt for abutting the corresponding patient facing surface 21 of the imaging platform cover 19 so as not to slide during operation. The lip may be in the order of ⅜ inches in height. The bottom edges of the skirts may have a high friction material coated thereon. In all other respects and in the use thereof, the device 126 is substantially the same as the device 26 heretofore described.

A further embodiment of the invention is illustrated in FIG. 5 which provides an even greater magnification than the device 126. Here the device 236 has a substantially larger base 228 and a substantially pyramid configuration, the height of the base being approximately eight inches from the bottom edge of all but the rear skirt 232, the rear skirt 232 having a downwardly depending portion 250 extending beneath the bottom surfaces of the other skirts. Wings 260, 262 extending outwardly from the end skirts 234, 236, intermediate the edge of the portion 250 and the lower edges of the skirts 234, 236 and having respective forwardly facing extensions 264, 266 permit the device to be positioned on the imaging table cover 19 and not only abut the rear of the platform but wrap slightly about the sides of the film cassette so that it is firmly in place when in use. Because of the substantially greater height of the base, the rear skirt 232 has a downward slope of approximately ¼ inch, i.e., a 1/32 grade. The opening 248 is approximately 3¾ inches by 1¼ inches to provide the required amount of depression to the rear of the upper surface 246 of the pedestal 240. With a device of these dimensions, the magnification is approximately 1.50.

Accordingly, the present invention provides a spot compression device which may be positioned on the imaging table above the x-ray film without being mechanically attached to the mammographic unit while in use. The device has a substantially rectangular base and a substantially circular pedestal of a truncated conical configuration, the slope of the cone being minimal. An opening is provided in the rear skirt of the rectangular base to increase the flexibility of the device and permit a greater degree of compression of the posterior aspect of a breast being x-rayed by permitting a relatively greater thinning of the breast at the nipple and subareolar area. The air gap provided between the flat upper surface of the pedestal, and thus between the breast and the imaging platform, provides improved contrast resolution and magnification By being interposed between the breast and the imaging platform the devices of the present invention not only may be utilized with any of the known mammographic units, but because a breast has a greater slope at the upper portion than at the lower portion, may provide greater clarity to the image than conventional spot compression paddles.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A spot compression and magnification device positionable on the surface of an imaging platform means of a mammographic apparatus for aiding in the spot compression of a breast of a female patient to provide x-ray images of localized portions of the breast, said device comprising a base having a polygonical cross sectional configuration including an upper platform and an open bottom defined between upstanding peripheral planar skirts, an aperture formed in said upper platform adjacent the plane of one of said skirts, an upstanding pedestal extending from said platform superposed about said aperture, said pedestal having an upstanding peripheral wall of a substantially circular configuration and a flat top surface adapted for receiving the lower portion of said breast, said pedestal being open at the bottom so that an air gap is formed between said top surface and the surface of said imaging platform means, said one skirt having means defining an opening formed therein for providing flexibility to said device to permit said pedestal to be depressed in the vicinity of said one skirt, and said pedestal having a flat surface adjacent said plane of said one skirt for abutting the chest of the patient when said breast is disposed on said flat top.

2. A spot compression and magnification device as recited in claim 1, wherein said device comprises a transparent synthetic plastic material having low x-ray absorptivity.

3. A spot compression and magnification device as recited in claim 1, wherein said pedestal has a substantially truncated conical configuration.

4. A spot compression and magnification device as recited in claim 1, wherein said base has a substantially rectangular cross sectional configuration.

5. A spot compression and magnification device as recited in claim 4, wherein at least said one skirt diverges from said platform to the bottom of said one skirt.

6. A spot compression and magnification device as recited in claim 2, wherein said pedestal has a substantially truncated conical configuration.

7. A spot compression and magnification device as recited in claim 6, wherein said base has a substantially rectangular cross sectional configuration.

8. A spot compression and magnification device as recited in claim 7, wherein said opening extends downwardly from adjacent said platform to the bottom of said one skirt.

9. A spot compression and magnification device as recited in claim 7, wherein said opening has a border wholly confined within said on skirt.

10. A spot compression and magnification device as recited in claim 9, wherein at least one skirt diverges from said platform to the bottom of said on skirt.

11. A spot compression and magnification device as recited in claim 1, wherein said flat surface of said pedestal diverges from said flat top toward said platform.

12. A spot compression and magnification device as recited in claim 11, wherein said pedestal has a substantially truncated conical configuration.

13. A spot compression and magnification device as recited in claim 12, wherein said base has a substantially rectangular cross sectional configuration.

14. A spot compression and magnification device as recited in claim 13, wherein said device comprises a transparent synthetic plastic material having low x-ray absorptivity.

15. A spot compression and magnification device as recited in claim 13, wherein at least said one skirt diverges from said platform to the bottom of said one skirt.

16. A spot compression and magnification device as recited in claim 15, wherein said opening extends downwardly from adjacent said platform to the bottom of said one skirt.

17. A spot compression and magnification device a recited in claim 15, wherein said opening has a border wholly confined within said one skirt.

18. A spot compression and magnification device as recited in claim 17, wherein said base has a substantially pyramid configuration.

19. A spot compression and magnification device as recited in claim 4, wherein said one skirt is longer than the remaining skirts for form a downwardly depending lip for abutting a corresponding patient facing surface of said imaging platform means.

20. A spot compression and magnification device as recited in claim 19, including wings extending outwardly from each end of said lip, each of said wings including a tab extending toward the plane of the skirt spaced from said one skirt, each tab being spaced from a respective skirt joining said one skirt.

21. In the method of performing spot compression of a breast of a female patient during a mammographic procedure using mammographic apparatus including imaging platform means within which x-ray sensitive film is carried for obtaining an x-ray of said breast, the improvement comprising: providing a spot compression and magnification device having a base and an upstanding pedestal including a flat top surface spaced from said base, said pedestal having a smaller cross sectional configuration than said base and said base having means for permitting depression of said pedestal when a force is applied on said pedestal, positioning said base on said image platform means, positioning the lower portion of said breast on said top surface of said pedestal, and applying a compression force to the upper portion of said breast to compress said breast against said pedestal.

22. In the method as recited in claim 21, wherein the step of providing a spot compression and magnification device includes selecting a spot compression and magnification device having a base of a selected height such that said flat top surface of said pedestal is spaced by a selected distance from said image platform means to provide a selected magnification of said image.

* * * * *